United States Patent
Ji et al.

(10) Patent No.: US 7,708,978 B2
(45) Date of Patent: May 4, 2010

(54) TARGETED HYDROPHILIC POLYMER, BINDERS WITH INTERFERON AND MEDICAL COMPOSITE COMPRISING ABOVE BINDERS

(75) Inventors: Shishan Ji, Beijing (CN); Dequan Zhu, Beijing (CN)

(73) Assignee: Beijing Jiankai Technology Co., Ltd., Beijing (CN)

( * ) Notice: Subject to any disclaimer, the term of this patent is extended or adjusted under 35 U.S.C. 154(b) by 817 days.

(21) Appl. No.: 10/514,492

(22) PCT Filed: Dec. 27, 2002

(86) PCT No.: PCT/CN02/00919

§ 371 (c)(1),
(2), (4) Date: Aug. 1, 2005

(87) PCT Pub. No.: WO03/095522

PCT Pub. Date: Nov. 20, 2003

(65) Prior Publication Data

US 2006/0014666 A1    Jan. 19, 2006

(30) Foreign Application Priority Data

May 14, 2002    (CN)    ............ PCT/CN02/00331

(51) Int. Cl.
*A61B 5/055*    (2006.01)
*A61K 38/14*    (2006.01)
(52) U.S. Cl. .......... 424/9.32; 424/9.414; 424/1.41; 424/1.73; 424/9.35; 514/8
(58) Field of Classification Search .......... None
See application file for complete search history.

(56) References Cited

U.S. PATENT DOCUMENTS 5,037,969 A * 8/1991 Minami et al. ........... 536/4.1

2002/0091288 A1 * 7/2002 Wilbur et al. ........... 564/505

FOREIGN PATENT DOCUMENTS

| EP | 0903152 A2 | 3/1999 |
|---|---|---|
| EP | 0950665 A1 | 10/1999 |
| GB | 600706 A | 4/1948 |
| GB | 816804 A | 7/1959 |
| JP | EP-0251304 A2 * | 1/1988 |
| WO | WO-01/00246 A2 * | 1/2001 |
| WO | WO 01/74399 A1 | 10/2001 |

OTHER PUBLICATIONS

Zalipsky, 1992, Polyethyleneglycol chemistry: Biotechnical and Biomedical Applications, Edited by Harris, Plenum Press, New York, 347-370.*
[Retrieved from] Website: http://home.att.net/~cat6a/org_chem-X.htm, 2009, 3 pages [retrieved on Jun. 18, 2009].*
Veronese, 2001, Biomaterials, 22, 405-417.*
Bailon, 1999, Third International Conference on Therapies for Viral Hepatitis, Abstract 79, p. 27.*
International Search Report of the International Searching Authority mailed Apr. 3, 2003 for international application No. PCT/CN02/00919, international filing date Dec. 27, 2002.

* cited by examiner

*Primary Examiner*—Andrew D Kosar
*Assistant Examiner*—Satyanarayana R Gudibande
(74) *Attorney, Agent, or Firm*—Finnegan, Henderson, Farabow, Garrett & Dunner LLP

(57) ABSTRACT

The present invention relates to an active targeted water-solubility macromolecule polymer, conjugate with interferon and pharmaceutical composition comprising the conjugate. The targeted agent includes, for example, glucose, galatose and the like, as well as their derivates. The conjugate of the present invention is well in water-solubility and have long physiological cycle half-life period, and have specific recognition to pathology organize, improved and increased medication effect of interferon to Hepatitis B, Hepatitis C etc. infectivity sickness and cancer, infect complication etc.

11 Claims, No Drawings

TARGETED HYDROPHILIC POLYMER, BINDERS WITH INTERFERON AND MEDICAL COMPOSITE COMPRISING ABOVE BINDERS

This application is the National Stage of International Application No. PCT/CN02/00919, filed Dec. 27, 2002, and claims the benefit of International Application No. PCT/CN02/00331, filed May 14, 2002.

FIELD OF THE INVENTION

The present invention relates to a targeted hydrophilic polymer, conjugate with interferon, and composition comprising the conjugate. The targeting agent in the invention is saccharide derivatives, such as amino-glucose, amino-galactose and the like.

BACKGROUND OF THE INVENTION

Interferons are a group of natural proteins that occur in the cell division process and exhibit anti-viral, antitumor, and immunomodulatory activities. The recombinant human interferon α and interferon β have been used as drugs for treatment of viral infections, cancer and multiple sclerosis. In the treatment of both hepatitis C and hepatitis B, interferon ox is the only effective agent on the market, and has become the standard therapy. However, because of its short circulation half-life (4-8 hours), their anti-viral activity and long-term treatment effect are limited. Recently, Schering-Plough and Hoffmann-La Roche have independently developed long-lasting interferon a formulations by conjugating with a synthetic water-soluble polymer. In 2001, Schering's product, PEG-intron®, obtained approval from the US FDA for treatment of hepatitis C. Roche's product, Pegasys®, had finished clinical studies and is waiting for the US FDA's approval. In WO01/74399A1, a targeted system using galactose-PEG was disclosed. Although it can obtain the effect of targeting toward the suffered tissue for interferon, but the measures for applying it are very complicated and difficult to meet the industrial needs. In addition, the polymer cannot be conjugated with interferon in an aqueous phase, and the conjugation must be catalyzed with enzyme.

Polyethylene glycol has been widely used in the field of protein conjugation. The resulting conjugates will improve in vivo circulation half-lives, and reduce immunogenecity and toxicity for proteins, peptides and other therapeutics. In both PEG-intron® and Pegasys®, polyethylene glycol not only improves their anti-viral efficacy but also reduces their injection frequency from three times a week to once a week.

However, neither PEG-intron® nor Pegasys® can achieve greater than 60% patient sustained response rate. Especially for hepatitis C virus of genotype I, sustained response rate is lower than 42%. To further improve the efficacy of interferon, it is believed that targeted delivering more interferon to the virus infected tissues or organs could be very beneficial.

In the researches of glycobiology, many bio-macromolecules on the cell surface are glycosylated compounds, also referred to glycoconjugate. They can be further classified into three types: glycoproteins, protcoglycans and glycolipids. Glycosylated compounds with extending oligosaccharides are the typical components anchored on the surface of cell membrane, cell wall and organella. The extending sugar parts have functions of information coding, which play very important roles in cell-cell recognition. For example, the recognition between a sperm and an egg in reproduction process is modulated by the sugar-protein interactions.

Polysaccharides are not the direct products of gene transcription, but their biosynthesis is adjusted by post translation. When there is a defect in the cell adjusting mechanism (such as in auto-immune diseases, cancer or other gene-related diseases), sugar synthesis and degradation are altered, resulting in changes in the component and composition of the sugar on the cell surface, leading to the alternation of the whole immune system. Comparing to amino acids, nucleotides, and fatty acids, the structures of saccharides are more complicated. For example, two different amino acids can produce two kinds of dipeptides, while two monosaccharides can produce eleven kinds of disaccharides. Three amino acids can produce six kinds of tripeptides, while three monosaccharides can lead to 1,056 kinds of trisaccharides. It is due to the branching properties of saccharide structure, which differs polysaccharides from other bio-macromolecules (such as proteins and polynucleotides). Based on its inherent structural complication, polysaccharides have become the carriers of detailed biological information, playing an important role in cell recognition and signal transduction.

Liver cancer is one of the common malignant cancer. Very few patients can be treated with surgical removal, and at same time, chemical and radical therapies have very low response rate. In China, liver cancer results in 100,000 deaths every year, and becomes the leading death cause in some parts of China. The major aim of the present invention is to improve the efficacy and lasting effect of the medicines toward liver diseases.

The asialoglycoprotein receptor (ASGPR) is a trans-membrane glycoprotein only existing on the liver cells of mammals. ASGPR can specifically recognize and then binds with the glycoproteins having a galactose unit at the terminal. The formed ligand-receptor complex can then be internalized into lysosome, and the macromolecule can be release a ASGPR itself will not be degraded, but recycle back to the surface of the cell membrane to participate into next cycle of transportation. Because of its specific property, ASGPR is also called liver specific galactose (H-Gal) receptor.

It is believed that with the combination of targeting agent and hydrophilic polymer, the interferon level at the infected tissues and organs will be increased, which will improve the anti-virus effect and achieve an improved treatment efficacy. In the treatment of hepatitis C and B, the efficacy of interferon will be significantly increased by extending its circulation half-life with PEGs and redirecting its distribution in the body, especially in the liver by the targeting agents. As a result, it is expected that anti-viral efficacy for treatment of hepatitis C and hepatitis B will be increased.

SUMMARY OF THE INVENTION

Therefore, one objective of the present invention is to provide an activated targeting hydrophilic high-molecular weight polymer derivatives represented by the following formula, which can react with protein (e.g. interferon) in an aqueous phase without enzymes or other catalysts:

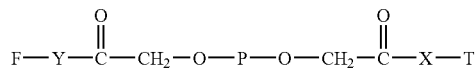

wherein:

X and Y are linking groups, selected from NH and O;

P is a hydrophilic polymer having an average molecular weight more than 18 Kda;

T is a targeting agent of a saccharide or its derivatives; and

F is an activating group, which can react with amino or thiol groups of the proteins in an aqueous phase without enzymes or other catalysts.

In a preferred embodiment of the invention, the activated targeting hydrophilic high-molecular weight polymer derivatives are represented as follows:

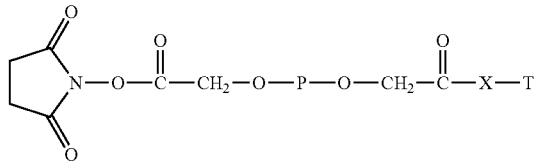

wherein:

X is a linking group selected from NH or O;

P is a hydrophilic polymer having an average molecular weight more than 18 Kda;

T is a targeting agent of a saccharide or its derivatives, such as glucose, galactose and the like.

In another aspect of the invention, there is provided a conjugate of the targeting hydrophilic polymer and an interferon molecule represented as follows:

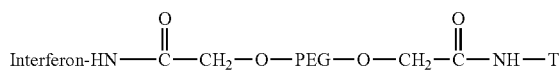

wherein:

PEG is a polyethylene glycol having an average molecular weight more than 18 kDa;

T is a targeting agent of a saccharide or its derivatives, such as glucose, galactose and the like;

Interferon is a protein of interferon family.

In the invention, the interferon can be either of α-, β- or γ-interferon.

In the invention, the targeting agent is of a saccharide or its derivatives, including monosaccharide such as glucose, mannose, galactose, lactose and fructose, and their oligomers.

In the invention, the hydrophilic polymer is selected from a polyethylene glycol, a polypropylene glycol, a polyvinyl alcohol, a polyacrylmorpholine and the copolymers thereof. Among them, a polyethylene glycol is preferred.

In the invention, the activated group F is selected from the group consisting of an ester group, a carbonate group, an amide group, an amido ester group, an ether group, a cabamate group, an acetal group and the like.

In one aspect of the invention, there is provided a pharmaceutical composition comprising the conjugate according to the invention. The composition can be used for treatment of infectious diseases such as hepatitis C and hepatitis B, cancer and infective complications through subcutaneous or intravenous injection.

The conjugate according to the present invention includes a high molecular weight hydrophilic polymer and at least one targeting agent. The high molecular weight hydrophilic polymer will provide an extended circulation half-life, while the targeting agent will lead interferon to the disease tissues. In the treatment of hepatitis C and hepatitis B, the targeting agents can be saccharide derivatives or antibodies targeting toward liver. Therefore, in the present invention, the conjugate of the polymer and interferon will not only provide prolonged circulation half-life, but also improve the interferon concentration around the infected liver tissues. It could significantly improve the treatment efficacy for hepatitis C than the current PEG-interferon conjugates.

DETAILED DESCRIPTION OF THE INVENTION

The present invention utilizes galactose property which can be specifically recognized and binded by liver surface asialoglycoprotein receptor (ASGPR), to further develop liver targeted drug delivery system.

In the present invention, the targeted conjugate can be prepared as follows: the hydrophilic polymer is modified to introduce a targeted agent and a activated functional group into different terminals of the polymer, and then the activated polymer is conjugated with an interferon, such as α-, β- or γ-interferon. Hereafter, PEG is used as an example of the hydrophilic polymer to illustrate the present invention. It should be understood that the hydrophilic polymer in the conjugate of the present invention can not be limited to a polyethylene glycol and its copolymer, it also can be a polypropylene glycol, a polyvinyl alcohol, a polyacrylmorpholine or the copolymers thereof.

The general structure of PEGs is shown as the formula below:

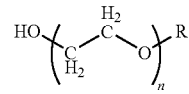

wherein:

R is H or a $C_{1-12}$ alkyl group; and n is an integer, representing the degree of the polymerization.

In respect of PEGs, they are usually measured by molecular weight. It is preferred that the molecular weight of PEG which forms the conjugates falls in the range from 300 to 60000 Daltons, which means n is about 6 to 1300. It is more preferred that n is 28, 112 and 450, respectively corresponding to molecular weight of 1325, 5000, and 20000. Because of the potential non-homogeneity of the starting PEGs which are usually defined by their molecular weights rather than the self-repeating unit n, PEGs are normally characterized with a weight average molecular weight, rather than their self-repeating units represented by n. The starting PEG compounds with different molecular weights are readily synthesized using methods known in the art or they are commercially available.

In addition of a linear polymer, polymers having a branched or other structure, such as Y shape, U shape and the like, can also be used for the modification of an interferon molecule. The structure of the polymer may be chosen depending on the properties of the pharmaceutical molecules.

In the present invention, the targeted hydrophilic polymer is based on a polyethylene glycol as a staking material, and is synthesized by binding a targeted agent, such as glucose, mannose, galactose, lactose and fructose, to the PEG according to any synthetic method well known to the skilled person in the art. In the practice, one terminal group of a PEG is activated first, and then reacts with an amino group or a hydroxyl group of a saccharide molecule. At the other end of a PEG, activation will be done to ensure that the targeted polymer system can react with drug molecules to form conjugates.

A carboxyl group is a common functional group for the PEG activation. There are many ways to incorporate a carboxyl group into a PEG. For example, an $OCH_2COOH$ structure at the terminal of PEG can be obtained as follows. This functional group can form an active ester that can easily reacts with an amino group or a hydroxyl group present in a sugar unit.

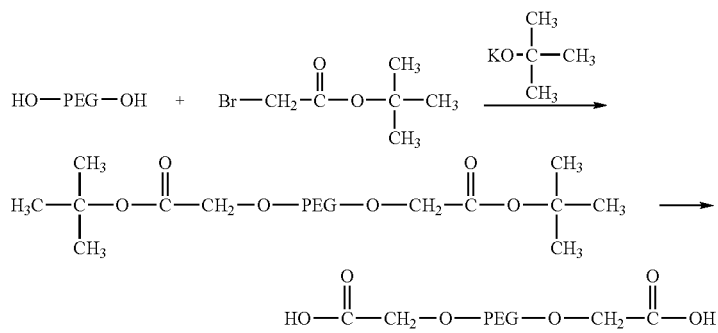

Also, an OCOOH functional group can be obtained as follows:

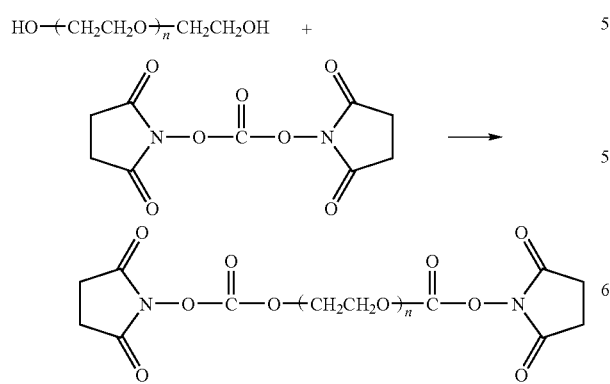

In the process of conjugating a saccharide molecule, N-hydroxyl succinimide (NHS) can be used to activate the carboxylic group. The ester of N-hydroxyl succinimide has a high reactivity toward an amino group to form a corresponding amide.

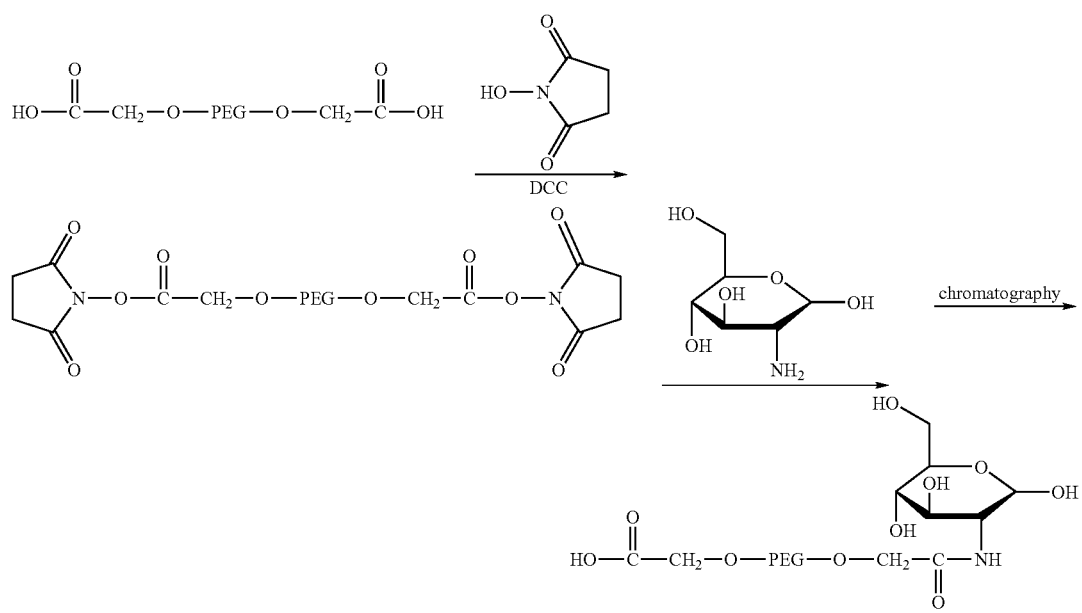

After reaction, it is necessary to isolate and purify the product. An anion exchange resin may be used to obtain the desired compound.

The conjugates of the present invention can be administered in the form of pure compounds or suitable pharmaceutical compositions, via any acceptable routes or being included in a reagent for similar use. Thus, the conjugates can be administered via oral, nasal, parenteral, topical, transdermal, rectal or injection routes in the form of solid, semisolid, lyophilized powder or liquid, for example, tablets, suppositories, pills, soft and hard gelatin capsules, powder, solution, suspension and aerosols. Preferably the unit dosage form is suitable for a precise-dosage and easy administration. The composition includes conventional pharmaceutical carriers or excipients and the conjugate(s) of the present invention as the active ingredient(s). Furthermore, it also can include other agents, carriers and excipients.

Generally speaking, depending on the method of administration, the pharmaceutically acceptable compositions will include about 1-99 wt. % of the conjugate of the present invention, and 99-1 wt. % of any suitable pharmaceutical excipient. Preferably they include 5-75 wt. % of the conjugate and the rest is any suitable pharmaceutical excipient.

The preferable way of administration is injection with a general daily dosage scheme, which can be adjusted based on the severity of the disease to be treated. The conjugates of the present invention or their pharmaceutically acceptable salts may be formulated in the dosage for injection by, for example, dissolving 0.5-50% of the active components in a liquid pharmaceutical carrier, such as water, saline, aqueous glucose, glycerol, ethanol and the like to form a solution or suspension.

The compositions which can be administered as liquid such as solutions and suspension can be prepared by dissolving and dispersing the conjugate of the present invention (about 0.5-20%) and optionally a pharmaceutical excipient into a carrier. Example of carriers includes water, saline, aqueous glucose, glycerol, ethanol and the like.

If needed, the pharmaceutical composition of the present invention can further include an adjuvant in a small amount, such as a wetting agent, an emulsifier, a pH buffer, an antioxidant and the like. For example, citric acid, sorbitan monolaurate, triethanolamine oleate, butylated hydroxytoluene and the like can be added.

The practical preparation methods of such dosage forms are known or obvious to the skilled in the art. For example, see Remington's Pharmaceutical Sciences, 18$^{th}$ edition, (Mack Publishing Company, Easton, Pa., 1990). In any case, according to the techniques of the present invention, the composition applied will include an effective amount of the conjugate of the present invention for the treatment of corresponding disease.

EXAMPLES

The polymer derivatives and the conjugates of the present invention and their preparation methods will be further described by the following examples. These examples do not intend to limit the scope of the invention by any means. The scope of the present invention can be determined by the claims.

Example 1

Preparation of Polyethylene Glycol Diethyl Acid

In an azeotropic distillation device, poly(ethylene glycol) of Mw 20000 (PEG20000, 100 g, 5 mmole) was dissolved in 500 ml of benzene at 50° C. and refluxed under $N_2$. After two hours, tbe solution was distilled to about 300 ml and was then cooled to 35° C. To the solution was added potassium tert-butoxide (50 mmole) dissolved in a mixed solvent of tert-butanol (100 ml) and benzene (50 ml). The mixture was stirred for two hours. To the mixture was added tert-butyl bromoacetate (60 mmole). The resulting solution was stirred under $N_2$ at room temperature overnight. The formed salt was then removed by filtration, the filtrate was concentrated by rotary evaporation, and the residue was then added into 500 ml of isopropyl alcohol (IPA). The precipitate was collected by filtration and dried under vacuum. The dried solid was dissolved into a basic solution of pH 12.0, and the solution was stirred overnight to complete hydrolysis. The pH of the solution was adjusted to 2.5 by addition of 1 N aqueous HCl solution, and the solution was extracted three times with 200 ml of methylene chloride. The combined organic phases were dried over anhydrous sodium sulfate, filtered, concentrated on a rotary evaporator, and then poured into 500 ml of IPA. The product was collected by filtration and dried under vacuum. Yield 90 g (90%). NMR (DMSO): δ3.5 (H in PEG, br m), 4.00 (2H, s).

Example 2

Preparation of Glucosamine-Polyethylene Glycol Ethyl Acid

PEG20000-bis-acid (80 g, prepared in Example 1) was dissolved in 500 ml of anhydrous methylene chloride. To the solution was added 1.0 g of n-hydroxysuccinimide (NHS) and 2.0 g of dicyclohexylcarbodiimide (DCC). The solution was stirred at room temperature overnight. The solution was filtered and the solvent was removed by rotary evaporation. The residue was added to 300 ml of isopropyl alcohol (IPA). The precipitate was collected by filtration, washed with 20 ml of diethyl ether and dried under vacuum. Yield 72 g (90%). NMR(DMSO): δ3.5 (H in PEG, br m), 4.60 (2H, s), 2.81 (4H, s).

The PEG20000-bis-acid NHS ester (70 g) was dissolved in 200 ml of anhydrous methanol. To the solution was added 1 g of glucosamine and 1 ml of dried triethylamine (TEA). The solution was stirred at 35° C. over night. The solvent was removed under vacuum at temperature below 35° C. To the residue was added 250 ml of sodium carbonate solution (5 wt %). The solution was stirred overnight. The pH of the solution was adjusted to 3 with HCl solution (1 N), and the solution was extracted three times with 300 ml of methylene chloride. The combined organic phases were dried over anhydrous sodium sulfate, filtered, concentrated on a rotary evaporator, and then precipitated into 500 ml of IPA. The product was collected by filtration and dried under vacuum. Yield: 61 g (87%).

The mixture of glucosamine-PEG20000-acids (30 g) was dissolved in deionized water and separated via an anion-exchange column. The fraction of glucosamine-PEG20000-monoacid was collected. Yield: 15 g (50%). Melting point: 60-64° C.

Example 3

Preparation of N-Hydroxyl Succinimide Glucosamino-Polyethylene Glycol-Mono Acid Ester (I)

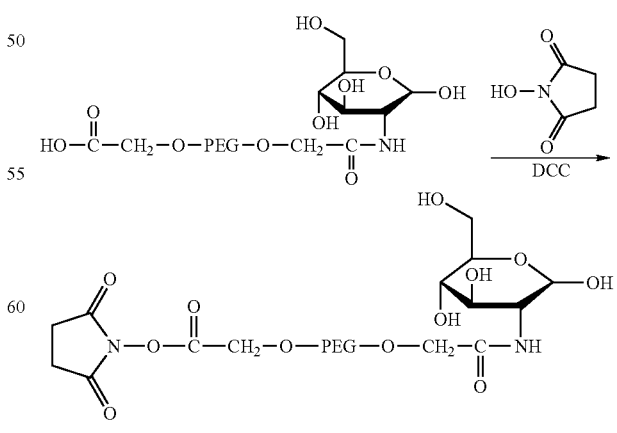

I

Glucosamine-PEG20000-mono-acid (from Example 2) (8 g) was dissolved in 80 ml of anhydrous methylene chloride. To the solution was added 50 mg of N-hydroxysuccinimide (NFS) and 95 mg of dicyclohexylcarbodiimide (DCC). The solution was stirred at room temperature overnight. The solution was filtered and the filtrate was concentrated by rotary evaporation. The residue was added to 150 ml of isopropyl alcohol (IPA). The precipitate was collected by filtration, washed with ethyl acetate and dried under vacuum. Yield 7.5 g (94%). NMR (DMSO): δ3.5 (H in PEQ br m), 4.60 (2H, s). 2.81 (4H, s).

Example 4

Preparation of N-Hydroxyl Succinimide Galactosamine-Polyethylene Glycol-Mono Acid Ester (II) acid ester (11)

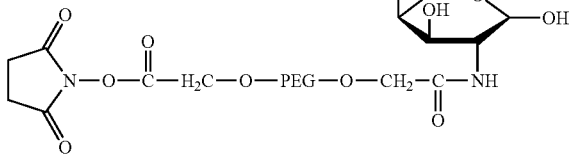

The procedures as described in Examples 2 and 3 were repeated with an exception that galactosamine was used instead of glucosamine.

Example 5

Preparation of N-Hydroxyl Succinimide Galactosamine-Polyethylene Glycol-Mono Acid Ester and α-Interferon N-hydroxyl succinimide galactosamine-polyethylene glycol-mono acid ester (II, molecular weight 20,000) was dissolved in 5 ml of buffered α-interferon solution with interferon concentration of 5 mg/ml (pH 7.4). In the reaction solution, N-hydroxyl succinimide galactosamine-polyethylene glycol-mono acid ester and α-interferon were mixed at a ratio of 5:1. The solution was shaken for 3 hour at room temperature. The pH of the solution was adjusted to 4.5 and the solution was diluted to an α-interferon concentration of 0.5 mg/ml, and purified by cation-exchange chromatography. The fraction containing the conjugate of mono-substituted galactosamine-polyethylene glycol-α-interferon was collected. SDS-PAGE showed that the product contained no free α-interferon.

Example 6

This example is to illustrate the preparation process of a typical pharmaceutical composition administered parenterally. The composition comprises the conjugate prepared in Example 5.

| Composition | |
|---|---|
| The conjugate of α-interfeon | 50 mg |
| 0.9% saline | to 10 ml |

The conjugate of α-interferon (the conjugate of mono-substituted galactosamine-polyethylene glycol-α-interferon) was dissolved in 0.9% saline to obtain 10 ml solution for subcutaneous or intravenous injection, which was filtered through 0.2 μm membrane and packed aseptically.

What is claimed is:

1. An activated targeting hydrophilic high-molecular weight polymer derivative having the following formula:

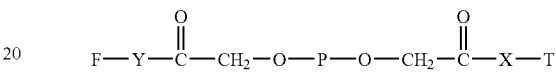

wherein:
X and selected from NH and O;
Y is O;
P is selected from polyethylene glycols, polypropylene glycols, and copolymers thereof, wherein P has an average molecular weight more than 18 kDa;
T is a targeting agent selected from glucosamine, glucose, mannose, galactose, lactose, fructose, and oligomers thereof; and
F taken together with 'Y' form an activated ester group.

2. An activated targeting hydrophilic high-molecular weight polymer derivative having the following formula:

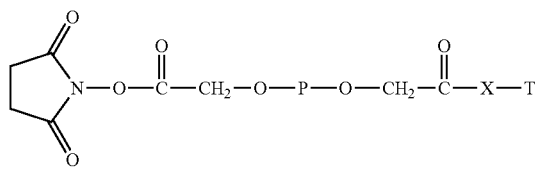

wherein:
X is a linking group-selected from NH and O;
P is selected from polyethylene glycols, a polypropylene glycols, and copolymers thereof, wherein P has an average molecular weight more than 18 Kda; and
T is a targeting agent selected from glucosamine, glucose, mannose, galactose, lactose, fructose, and oligomers thereof.

3. The hydrophilic high-molecular weight polymer of claim 1, wherein the polyethylene glycol has an average molecular weight of 18,000 to 50,000.

4. A conjugate of a targeting hydrophilic polymer and interferon having the following formula:

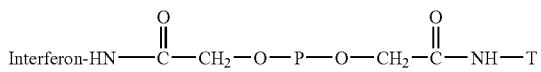

wherein:
T is a targeting agent selected from glucosamine, glucose, mannose, galactose, lactose, fructose, and oligomers thereof;

P is selected from polyethylene glycols, polypropylene glycols, and copolymers thereof, wherein P has an average molecular weight more than 18 kDa; and Interferon is a protein of interferon family.

5. The conjugate of claim 4, wherein the polyethylene glycol has an average molecular weight of from 18,000 to 50,000.

6. The conjugate of claim 4, wherein the interferon is α-, β- or γ-interferon.

7. A pharmaceutical composition comprising a conjugate according to claim 4 and a pharmaceutically acceptable carrier or excipient.

8. The composition of claim 7, wherein it is formulated into the form for injection or of solution, tablet, suspension and aerosol.

9. The composition of claim 8 for the treatment of hepatitis C and hepatitis B, or cancer.

10. The composition of claim 7, wherein the polyethylene glycol has an average molecular weight of from 18,000 to 50,000.

11. The composition of claim 7, wherein the interferon is α-, β- or γ-interferon.

* * * * *